United States Patent
Herod et al.

(10) Patent No.: US 6,847,443 B1
(45) Date of Patent: Jan. 25, 2005

(54) SYSTEM AND METHOD FOR MULTI-WAVELENGTH, NARROW-BANDWIDTH DETECTION OF SURFACE DEFECTS

(75) Inventors: David W. Herod, Greenville, TX (US); Youling Lin, Richardson, TX (US)

(73) Assignee: Rudolph Technologies, Inc., Flanders, NJ (US)

( * ) Notice: Subject to any disclaimer, the term of this patent is extended or adjusted under 35 U.S.C. 154(b) by 0 days.

(21) Appl. No.: 10/322,582

(22) Filed: Dec. 18, 2002

Related U.S. Application Data
(60) Provisional application No. 60/350,308, filed on Jan. 17, 2002.

(51) Int. Cl.[7] ............................................... G01N 21/88
(52) U.S. Cl. ............................... 356/237.2; 356/237.1; 250/559.27
(58) Field of Search .......................... 356/237.1–237.6; 250/205, 559.26, 559.27, 559.4, 559.44, 559.19, 372; 362/11–12

(56) References Cited

U.S. PATENT DOCUMENTS

| | | | | |
|---|---|---|---|---|
| 5,493,123 A | * | 2/1996 | Knollenberg et al. ....... 250/372 |
| 5,758,942 A | * | 6/1998 | Fogal et al. ................... 362/12 |
| 5,777,729 A | | 7/1998 | Aiyer et al. |
| 5,822,055 A | * | 10/1998 | Tsai et al. ................. 356/237.1 |
| 6,166,801 A | * | 12/2000 | Dishon et al. ................. 355/27 |
| 6,423,977 B1 | * | 7/2002 | Hayasaki et al. ...... 250/559.19 |
| 6,452,671 B1 | * | 9/2002 | Uda et al. ................. 356/237.2 |
| 6,489,624 B1 | * | 12/2002 | Ushio et al. ........... 250/559.27 |
| 6,570,650 B1 | * | 5/2003 | Guan et al. .............. 356/237.4 |
| 6,633,831 B2 | * | 10/2003 | Nikoonahad et al. ....... 702/155 |

\* cited by examiner

*Primary Examiner*—Gregory J. Toatley, Jr.
*Assistant Examiner*—Sang H. Nguyen

(57) ABSTRACT

A system and method for detecting defects in surface structures, such as those formed on semiconductor wafers. A light source, preferably a strobe light, provides illumination that is separated by a filter into a plurality of selected bandwidths. The light then is transported through a fiber optic cable to a diffuser, and from there directed toward the surface. A camera captures a plurality of images, each image formed by a separate portion of the electromagnetic spectrum. The images may be formed by either reflected or diffracted light, or both. The images may be stored or compared to an image of a calibration wafer.

6 Claims, 8 Drawing Sheets

DIFUSE ILLUMINATION
TRIPLE WAVELENGTH
CONFIGURATION (NORMAL ILLUMINATION)

SYSTEM AND METHOD FOR MULTI-WAVELENGTH, NARROW-BANDWIDTH DETECTION OF SURFACE DEFECTS

RELATED APPLICATIONS AND CLAIM OF PRIORITY

This nonprovisional application claims priority based upon the prior U.S. provisional patent application No. 60/350,308, filed Jan. 17, 2002, and is related to U.S. patent application Ser. No. 10/094,119, filed Mar. 8, 2002, both of which are incorporated herein by reference in their entirety.

BACKGROUND OF THE INVENTION

1. Technical Field of the Invention

This invention relates to optical inspection systems. More particularly, and not by way of limitation, the present invention is directed to the automated optical inspection and analysis of regularly-patterned production surfaces such as those on semiconductor wafers, using multi-wavelength, narrow-bandwidth imaging.

2. Description of Related Art

Optical inspection of articles of manufacture, either finished or in-process, may range from simple visual inspection to sophisticated computer-assisted inspection. Automated inspection is increasingly valuable as equipment and techniques improve because it is fast, reliable, and can frequently detect production defects that cannot be easily perceived by the unaided human eye.

This is true in the case of the in-process inspection of semiconductor wafers. Semiconductor wafers are manufactured in stages, with each stage representing the development of a new layer, or set of surface structures that form a functional part of the electronic devices that will populate the wafer when it is finished. The structures of each stage are formed by selectively etching away or treating carefully selected areas of the surface. The selection of areas to be etched or treated is often accomplished by covering the remaining area with a protective material called photoresist.

The photoresist is first applied evenly to the entire wafer surface, then selectively exposed to light emitted through a mask. This changes the nature of the exposed area so that it becomes, for example, more or less soluble. Then during development, the exposed areas are either retained or washed away (depending on the type of photoresist used), leaving a pattern of resist structures that will protect the wafer surface under them as the remainder of the surface is altered. During the process of etching, for example, unprotected areas are removed to a certain depth, perhaps to be filled later or otherwise treated. The protective photoresist is then removed, leaving only the desired surface configuration. The next stage can then be prepared for treatment and the process repeated until the desired surface structures have been completely formed.

Frequent inspections of the wafer surface are desirable during the production process, especially at the point where photoresist structures have been formed. Although many types of defects can be repaired, the photoresist is relatively easily removed and reapplied, so it is most advantageous to detect defects in it, rather than etching an improperly treated wafer that would be more difficult and expensive to repair.

Wafers in the process of manufacture can, of course, and sometimes are visually inspected for defects. Generally, however, an automated inspection system is used. In such systems, some form of electromagnetic energy, often but not always visible light, is directed at the surface to be inspected. The image created by the light reflecting from the surface is then captured and translated into digital form for processing by a computer.

The surface-image data may, for example, be analyzed to determine if unusual or tell-tale patterns are present that are commonly associated with certain kinds of defects. In one such technique, called image decomposition, surface structures are traced and described in terms of image grammars composed of units called primitives. One such technique is explained in detail in co-owned and co-pending U.S. patent application Ser. No. 09/074,301, entitled SYSTEM AND METHOD OF OPTICALLY INSPECTING MANUFACTURED DEVICES, filed May 6, 1998, a continuation-in-part of U.S. patent application Ser. No. 08/867,156, which issued on Jul. 18, 2000 as U.S. Pat. No. 6,091,846, entitled METHOD AND SYSTEM FOR ANOMALY DETECTION, both of which are incorporated herein by reference in their entirety. In some systems, the images associated with each inspection are classified, stored, and indexed for later use. Comparisons may be made to detect errors in the defect-detection process itself and to analyze the manufacturing process in order to determine, if possible, the root cause of frequently discovered defects in the hope of minimizing the occurrence of similar defects in the future.

In some instances, capturing an image of light reflected specularly from the wafer surface is inadequate for efficient and comprehensive defect detection. It has been found, for example, that defects such as focus offset (defocus errors) due to the presence of stray particles, errors in wafer development, etching or stripping, or to insufficient developer, are sometimes detectable by examining the light diffracted from the structures on the production surface. However, some defocus errors are so small as to require a high resolution imaging capability, and existing systems do not detect such errors.

When, as is the case with a properly-constructed semiconductor wafer, an object's surface features are small and sufficiently uniform so as to form a regular pattern that amounts to or approximates a diffraction (or, more properly, a reflection) grating, an analysis of the diffracted light is also useful. One method of using diffracted light is disclosed in U.S. Pat. No. 5,777,729 to Aiyer et al. Aiyer uses an elongated and extended monochromatic light source to illuminate an entire wafer surface, with each point thereon being illuminated by light at different angles. A diffraction efficiency is then calculated and utilized for defect detection. Other methods of using diffracted light are disclosed in co-owned and co-pending U.S. patent application Ser. No. 10/094,119, filed Mar. 8, 2002, entitled SYSTEM AND METHOD FOR PERFORMING OPTICAL INSPECTION UTILIZING DEFRACTED LIGHT (claiming priority to U.S. Provisional Patent Application No. 60/278,961 entitled, METHOD OF PERFORMING OPTICAL INSPECTION, filed Mar. 27, 2001), and co-owned and co-pending U.S. patent application Ser. No. 10/298,391, filed Nov. 18, 2002, entitled OPTICAL INSPECTION METHOD UTILIZING ULTRAVIOLET LIGHT, both of which are incorporated by reference herein in their entirety.

The utilization of diffracted light, however, somewhat complicates the inspection process. For example, when monochromatic light is directed at a known angle of incidence at a particular area on the wafer surface for which the grating pitch (i.e., distance between the regular surface features) is known, it is possible to predict the angle of first- (or other-) order diffraction, since the angle(s) of diffraction are a function of the grating pitch and the angle of incidence. For a light source in a fixed position, the camera or other image-capturing device used must be repositioned each time the grating pitch changes in order to capture light exiting the surface at a particular order of diffraction. Additionally, for a fixed light source and fixed grating pitch, the camera must be repositioned to capture light exiting the surface at different orders of diffraction. Finally, if the wavelength of the incident light is changed, once again, the camera must be repositioned to capture light exiting the surface at any particular order of diffraction.

Another problem encountered in diffractive imaging is that some types of surface defects are more readily detected at a first range of wavelengths while other types of surface defects are more readily detected at a second range of wavelengths. Thus, monochromatic illumination at a particular wavelength may not provide the sensitivity required to detect defects that are more readily detectable at other wavelengths. Therefore, broad bandwidth illumination is required in order to provide imaging at all of the required wavelengths. The problem with this approach is that broad bandwidth illumination, in diffractive imaging systems, degrades both system contrast and sensitivity for detecting defocus errors.

In order to overcome the disadvantage of existing solutions, it would be advantageous to have a system and method for multi-wavelength, narrow-bandwidth detection and analysis of surface defects that does not degrade system contrast or defocus error detection sensitivity. The present invention provides such a system and method.

SUMMARY OF THE INVENTION

In one aspect, the present invention is directed to a system for multi-wavelength, narrow-bandwidth detection and analysis of surface defects. The system utilizes illumination in multiple wavelength ranges, but utilizes narrow-bandwidth illumination within each range. The center wavelength of each narrow-bandwidth illumination is selected to optimize the detection of particular types of defects. A multi-wavelength, narrow-bandwidth optical filter may be utilized to select and limit the illumination wavelengths. A multi-channel camera is utilized to capture the image. The spectral response of each camera channel and the narrow-band illumination wavelengths are matched so that the center wavelength of each narrow-bandwidth illumination range matches the wavelength where each camera channel has peak spectral response. System contrast and detection sensitivity are thereby enhanced.

For additional contrast and sensitivity, the system may include a collimator that collimates the incident multi-wavelength, narrow-bandwidth light. The surface of the wafer may be illuminated by incident light striking normal to the surface for reflective imaging, at an angle to the surface for diffractive imaging, or both. Defects are detected by measuring the amount of light that reaches the camera from each area of the wafer surface. By comparing the measured light levels with predefined light levels from a defect-free wafer, contrast levels are determined for each area of the wafer surface. The greater the contrast level, the larger the defect.

In another aspect, the present invention is directed to a method of multi-wavelength, narrow-bandwidth detection and analysis of surface defects. The system of the invention is utilized to capture images of a statistically significant number of wafers. For each wafer, contrast levels for detected defects are stored in a database. If a contrast level of a particular magnitude is detected more often than other contrast levels, then defects of a size associated with that contrast level occur more often in the wafer manufacturing process. A calibration wafer on which defects of known sizes have been imaged may be utilized to quantify the size of the defects. A calibration wafer may be created by microscopically measuring the size of particular defects for which the contrast level has been measured. Thereafter, the size of imaged defects can be determined by comparing the measured contrast levels with the levels recorded for the calibration wafer.

BRIEF DESCRIPTION OF THE DRAWINGS

The invention will be better understood and its numerous objects and advantages will become more apparent to those skilled in the art by reference to the following drawings, in conjunction with the accompanying specification, in which.

DETAILED DESCRIPTION OF EMBODIMENTS

The invention produces high contrast imaging using triple-wavelength, narrow-bandwidth illumination. The illumination may be diffuse or collimated, and may be angular diffractive illumination, illumination normal to the surface, or both. The imaging system provides a three channel analyzer using three filter wavelengths simultaneously. The resulting image is not a color photograph of the wafer surface, but is instead a color diagnostic map.

Experimentation has been conducted using single-wavelength, narrow-bandwidth illumination, i.e., using a single filter that centers around one particular wavelength. The filter allows light only of the particular wavelength (plus or minus some narrow bandwidth) to pass through. The present invention extends single-wavelength, narrow-bandwidth illumination and applies it to color imaging which requires illumination with three wavelengths in the visible spectrum—red, green, and blue. Other wavelengths such as ultraviolet or infrared may also be utilized within the scope of the present invention, but the exemplary embodiment described herein utilizes red, green and blue visible light.

Figure 1:
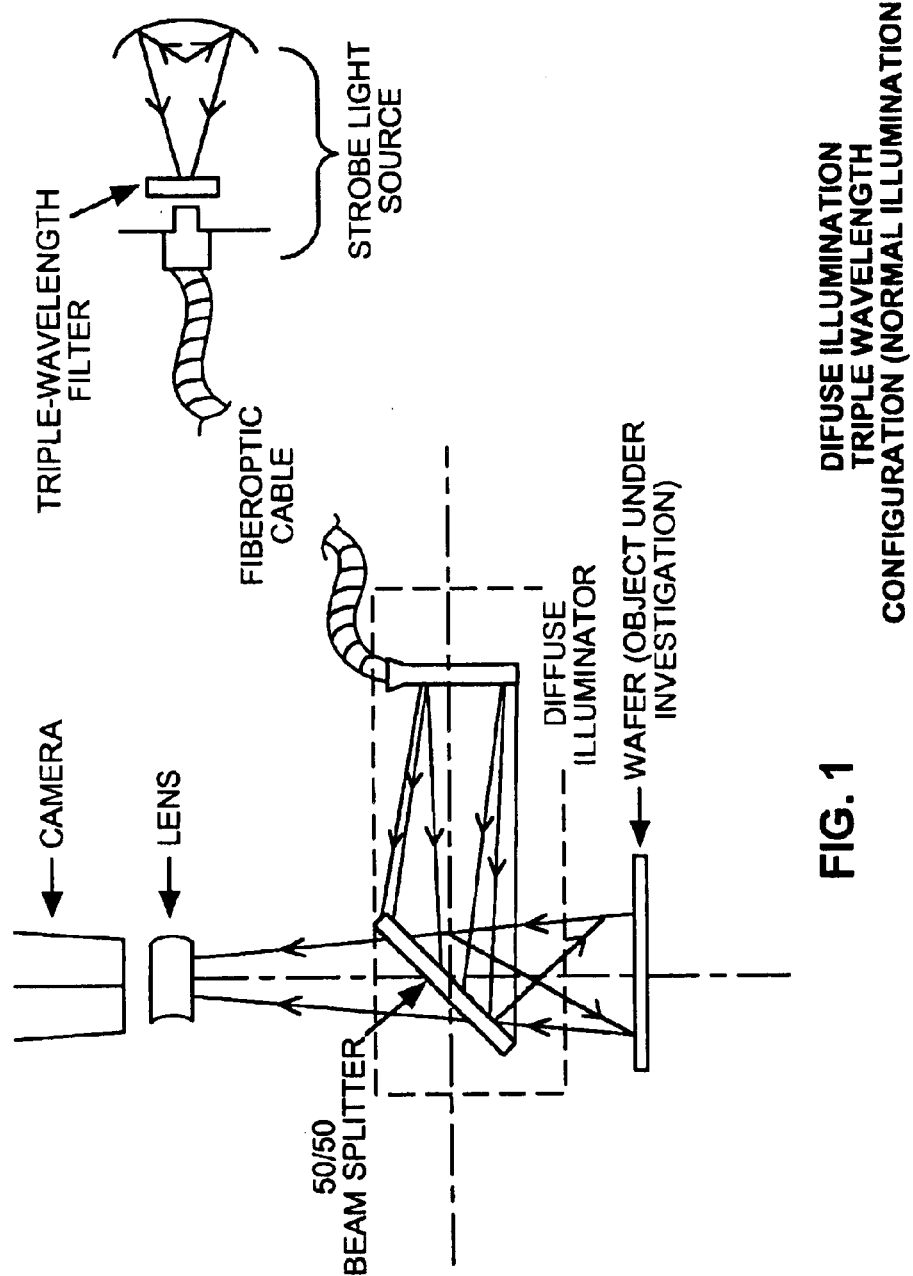
FIG. 1 is a simplified block diagram illustrating a configuration of the present invention in which triple-wavelength, narrow-bandwidth, diffuse illumination is utilized to strike an object under inspection normal to the surface.

FIG. 1 is a simplified block diagram illustrating a configuration of the present invention in which a triple-wavelength, narrow-bandwidth filter is utilized to produce triple-wavelength, narrow-bandwidth diffuse illumination. The illumination then strikes the surface of a semiconductor wafer normal to the surface. The light source for the present invention is a strobe light which is focused onto the triple-wavelength, narrow-bandwidth filter by a curved reflector (for example, an elliptical reflector). When using diffuse light, the multi-wavelength, narrow-bandwidth filtered light then passes through a coupling into a fiber optic cable which delivers the light to a diffuser. The object under inspection (in this case the wafer surface) is then illuminated with triple-wavelength, narrow-bandwidth diffuse illumination.

The triple-wavelength, narrow-bandwidth filter allows light to pass through only at discrete frequencies in the red, green, and blue wavelength ranges. Alternatively, three narrow-bandwidth filters, one in the red wavelength range, one in the green wavelength range, and one in the blue wavelength range may be utilized. The multi-wavelength, narrow-bandwidth filter is commercially available, and the specific frequencies to be passed through the filter can be specified to customize the filter as required. A suitable off-the-shelf triple-wavelength bandpass filter is Component XF3063, available from Omega Optical, Incorporated. The XF3063 filter has center frequencies at 460 nm, 520 nm, and 602 nm in the blue, green and red wavelength ranges, respectively.

Figure 5:
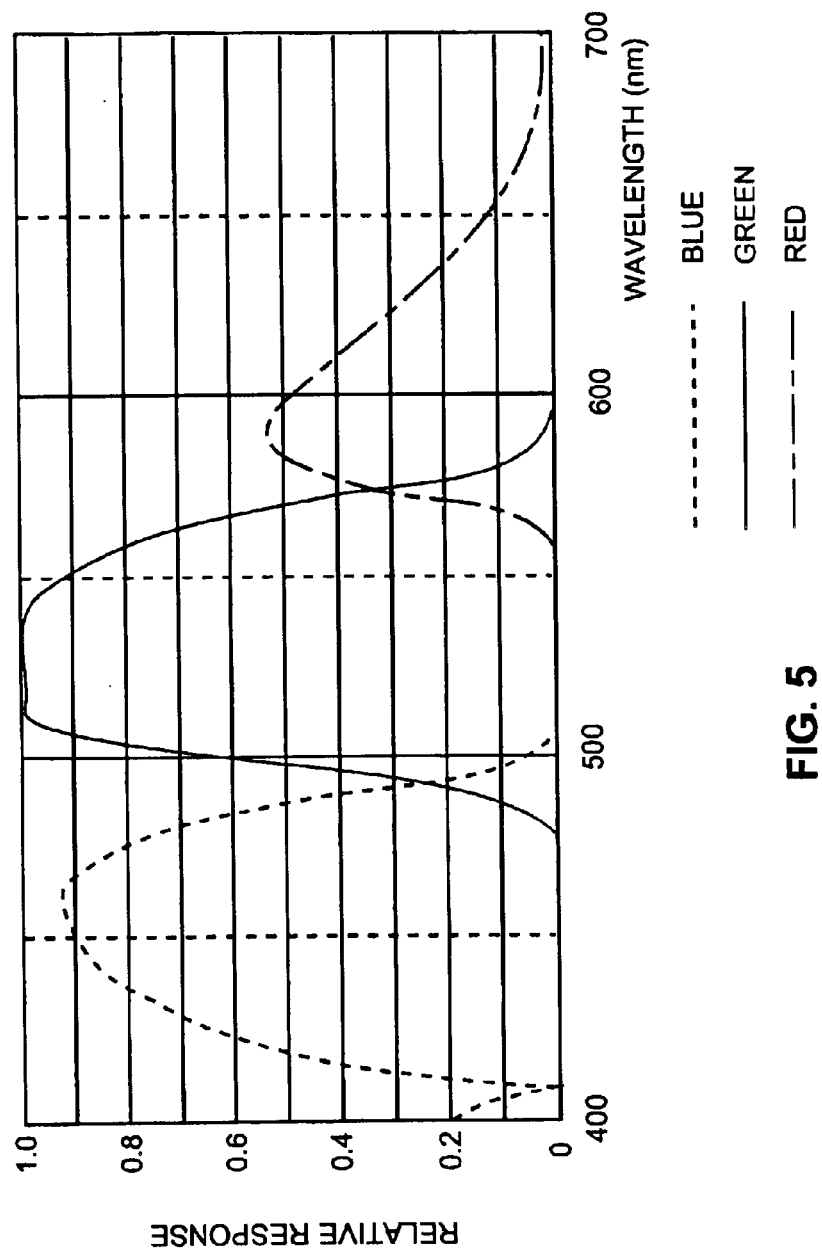
FIG. 5 is a spectral response graph illustrating the relative response level of each channel of a typical 3-channel CCD camera.

A multi-channel camera may be utilized to capture the image of the illuminated wafer surface. A suitable camera for the visible light spectrum is the Sony XC-003/P Charged-Couple Device (CCD) camera. The CCD camera has three channels. Each of the channels is sensitive over a relatively broad range, but the sensitivity in each color range has a peak. For the blue range, the sensitivity peaks at about 460 nm. For the green range, the sensitivity peaks at about 520 nm. For the red range, the sensitivity peaks at about 585 nm. The spectral response of the Sony XC-003/P CCD camera is shown in FIG. 5.

In one embodiment, the wavelengths for the multi-wavelength, narrow-bandwidth filter are chosen to match the wavelengths at which the spectral response for the three channels in the CCD camera are the greatest. Thus, when using the Sony XC-003/P CCD camera, the ideal multi-wavelength bandpass filter would pass narrow-bandwidth light centered at 460 nm, 520 nm, and 585 nm. Thus, the XF3063 filter, which passes narrow-bandwidth light centered at 460 nm, 520 mm, and 602 nm, is ideal for the blue and green wavelength ranges, and provides slightly degraded performance for the red range.

The configuration of FIG. 1 utilizes a 50/50 beam splitter to direct approximately 50% of the incident illumination onto the wafer, normal to the surface. When using the 50/50 beam splitter, the optical axes of the illumination system and the imaging system are the same.

Approximately 50% of the light reflected from the wafer surface then passes through the beam splitter a second time on its way to the CCD camera. Since the light passes through the 50/50 beam splitter twice, this results in only about 25% of the incident light reaching the camera. Since the triple-wavelength filter is filtering out all but three discrete wavelengths, the strobe light must be operated at a higher intensity to achieve the same level of illumination as achieved by full spectrum visible light. This may shorten the life of the bulb, the advantage gained through increased defect-detection sensitivity offsets the additional cost, if any.

The diffuse illuminator and 50/50 beam splitter may be housed in an enclosure such as a black box that has an opening for the fiber optic cable, an opening for the incident light to pass from the beam splitter to the wafer surface, and an opening for the light exiting the wafer surface to pass from the beam splitter to the camera.

The use of monochromatic narrow-bandwidth illumination provides, in effect, a single-channel analyzer while the use of three narrow-bandwidth illuminations, in three different color ranges, provides a three-channel analyzer. When using monochromatic narrow-bandwidth illumination such as a frequency in the blue range, only the blue channel in the CCD camera is active. The red and green channels are dark. Likewise, when using a narrow-bandwidth illumination in the red wavelength range, only the red channel in the CCD camera is active. The blue and green channels are dark. And so on. Thus, only one-third of the capacity of the color camera is being utilized. The present invention uses all three channels of the camera. As a result, color images are produced that are a combination of three narrow-bandwidth illuminations.

Thus, the invention applies narrow-bandwidth imaging in three separate channels to produce color images. The CCD camera simultaneously captures images at three discrete frequencies in three different wavelength ranges, and produces higher contrast images in those three wavelength ranges. The use of three narrow-bandwidth illuminations, in three different color ranges, increases the sensitivity across the whole visible spectrum and provides a three-channel analyzer. Some defects, show up better in red light than they do in blue or green light. Likewise, other defects show up better in blue light than they do in red or green, and still other defects show up better in green light than they do in red or blue. The use of narrow-bandwidth illumination in all three color ranges optimizes the sensitivity of the system to particular defects in the wavelength ranges that those defects produce the highest contrast. Thus, the sensitivity to a number of defect types is optimized.

When the entire wafer surface is scanned, the different defect types can be displayed simultaneously because they occur in different channels. In a particular area, if more signal is received in the blue range than in the red or green ranges, then the image is blue in that particular area. Instead of producing a photographic rendering of the surface (i.e., a faithful color representation of the surface), the invention produces a color defect map with different types of defects showing up in different colors since the individual defects on the surface affect the color.

Although the use of multi-wavelength, narrow-bandwidth illumination in the configuration of FIG. 1 provides a distinct increase in detection sensitivity, the use of diffuse light has the disadvantage that diffuse light travels in many different directions as it leaves the diffuser. Thus, after reflecting off of the 50/50 beam splitter, some of the light rays are not exactly perpendicular to the wafer surface, and may not reflect vertically to the camera. This has a negative impact on the sensitivity of the system.

Figure 2:
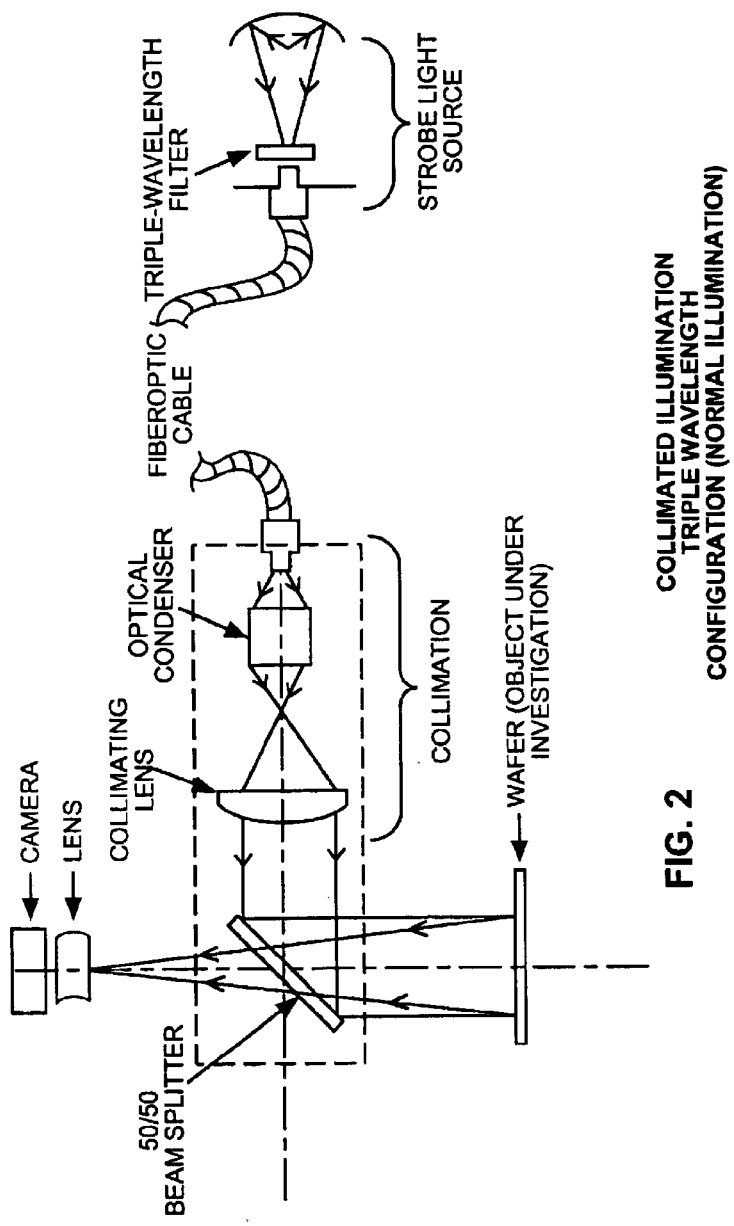
FIG. 2 is a simplified block diagram illustrating a configuration of the present invention in which triple-wavelength, narrow-bandwidth, collimated illumination is utilized to strike an object under inspection normal to the surface.

FIG. 2 is a simplified block diagram illustrating a configuration of the present invention in which triple-wavelength, narrow-bandwidth, collimated illumination is utilized to strike an object under inspection normal to the surface. The use of collimated illumination instead of diffuse illumination is another technique that the present invention utilizes to increase sensitivity. When using collimated light, the same lighting configuration may be utilized to supply multi-wavelength, narrow-bandwidth filtered light to the fiber optic cable. The cable then delivers the light to a collimator comprising an optical condenser and a collimating lens. The optical condenser takes the light from a relative large fiber optic cable and focuses it down to a very small area in order to provide more uniform illumination. The collimating lens then emits parallel rays of light that are sent to the 50/50 beam splitter where approximately 50% of the light is reflected onto the object normal to the surface. Since the light rays are parallel when they strike the 50/50 beam splitter, all of the reflected light rays are perpendicular to the surface, and reflect vertically to the camera. This increases the detection sensitivity of the system.

The optical condenser, collimating lens, and 50/50 beam splitter may be housed in an enclosure such as a black box that has an opening for the fiber optic cable, an opening for the incident light to pass from the beam splitter to the wafer surface, and an opening for the light exiting the wafer surface to pass from the beam splitter to the camera. The lens of the camera may be focused at or near infinity since the light rays entering the camera are either parallel or only slightly diffracted. The configuration of FIG. 2 provides an improvement in sensitivity over the configuration of FIG. 1 through the use of collimated illumination.

Figure 3:
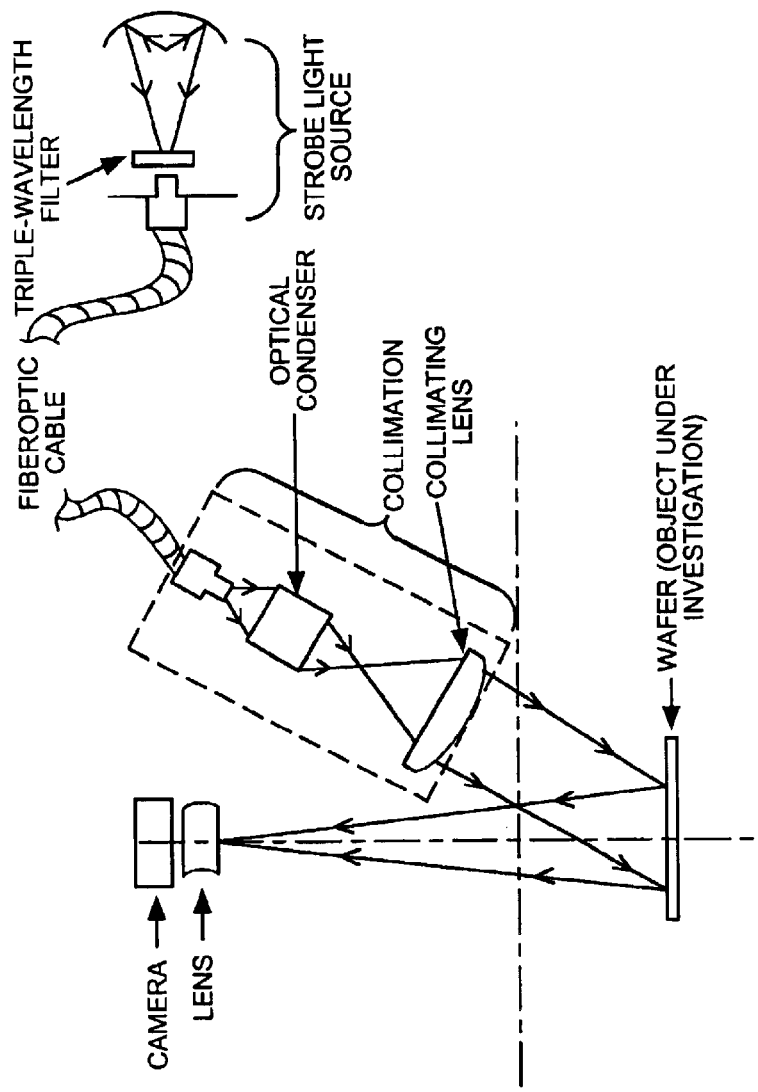
FIG. 3 is a simplified block diagram illustrating a configuration of the present invention in which triple-wavelength, narrow-bandwidth, collimated illumination is utilized to strike an object under inspection at an angle to the surface, creating diffracted light that is directed to the camera.

FIG. 3 is a simplified block diagram illustrating a configuration of the present invention in which triple-wavelength, narrow-bandwidth, collimated illumination is utilized to strike an object under inspection at an angle to the surface, creating diffracted light that is directed to the camera. The present invention can thus illuminate the wafer surface utilizing two different illumination methods. With triple-wavelength, narrow-bandwidth illumination, the surface can be illuminated with light normal to the surface using the 50/50 beam splitter, or with light at an angle. When the collimated illumination strikes the surface at an angle, diffracted light at one order of diffraction leaves the surface normal to the surface and goes up to the camera. Diffracted light is particularly useful for detecting defocus errors because even very small defocus errors cause a shift in the angle of diffraction, causing a decrease in the amount of light directed to the camera.

The diffraction order and other diffractive characteristics of the light are determined by the wafer surface. The wafer surface has a large number of small structures that have repetitive patterns and thus act as a diffraction grating to diffract the light. Differences in the angle of diffraction caused by defects in the wafer surface cause the level of light detected at the camera to vary. The detected light level is then compared to a predefined light level for a defect-free surface to obtain a contrast level. Larger defects cause greater differences in the detected light level and thus greater contrast levels. The configuration of FIG. 3 is strictly for diffraction imaging, and enhances the sensitivity through the use of the triple-wavelength filter and the collimated illumination. The disadvantage of this configuration is that it does not provide for illumination normal to the surface which is more efficient at detecting other types of defects.

Figure 4:
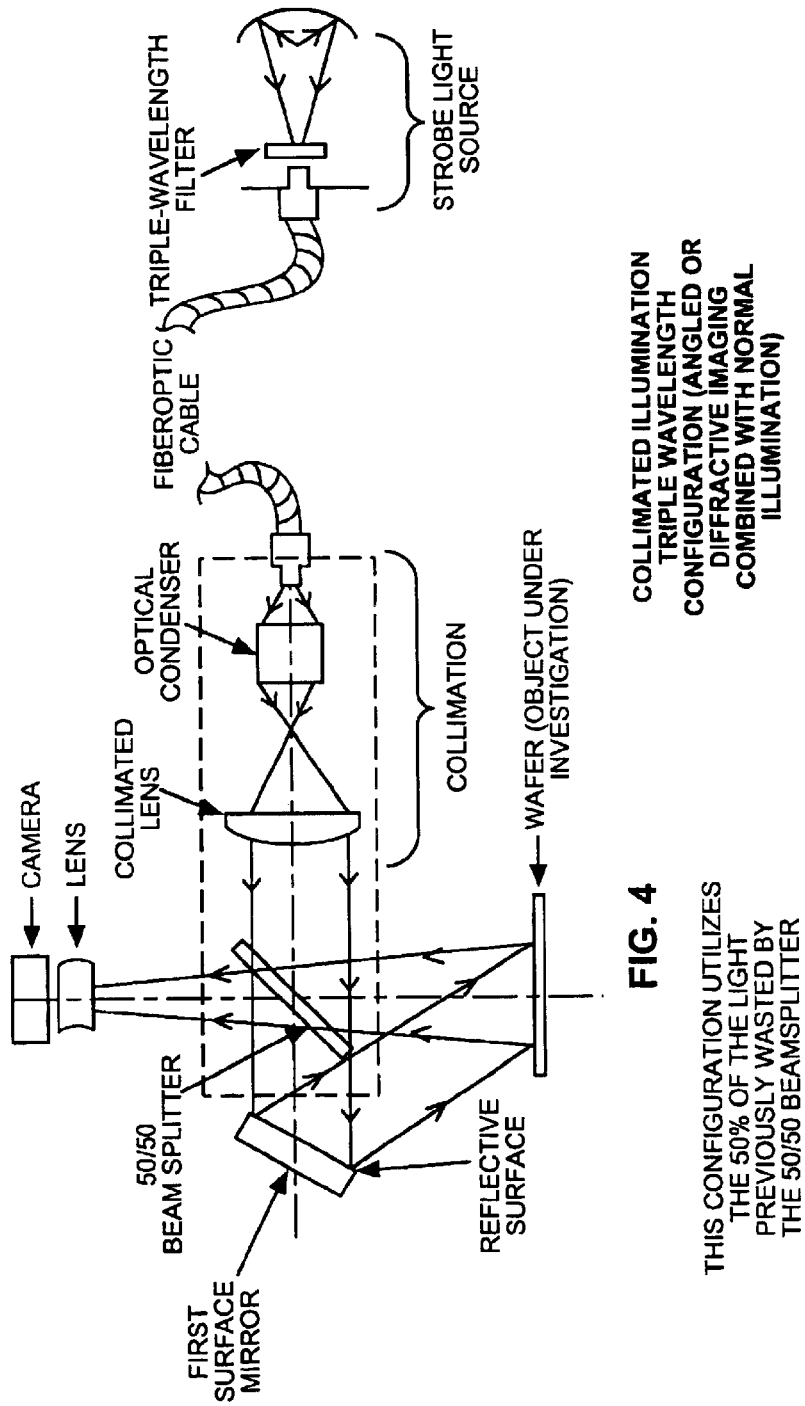
FIG. 4 is a simplified block diagram illustrating a configuration of the present invention in which triple-wavelength, narrow-bandwidth, collimated illumination is utilized to strike an object under inspection normal to the surface, and to also strike an object under inspection at an angle to the surface, creating diffracted light that is directed to the camera.

FIG. 4 is a simplified block diagram illustrating a configuration of the present invention in which triple-wavelength, narrow-bandwidth, collimated illumination is utilized to strike an object under inspection both normal to the surface, and also at an angle to the surface. This configuration directs both normally reflected light and diffracted light to the camera. All of the light that is generated by the light source and collimated by the collimator is directed onto the wafer surface. The 50/50 beam splitter directs 50% of the light onto the surface normal to the surface. The 50% of the light that passes through the beam splitter is reflected onto the surface at an angle by a first-surface mirror mounted behind the 50/50 beam splitter. Since a greater amount of light strikes the surface, and since some defects are more sensitive to light that strikes the wafer normal to the surface, and other defects such as defocus errors are more sensitive to light that strikes the wafer surface at an angle, the configuration of FIG. 4 has the greatest sensitivity for defect detection.

By using a first-surface mirror behind the 50/50 beam splitter, angled to reflect the light passing through the beam splitter onto the surface of the object at an angle, the present invention uses all three sensitivity enhancement techniques simultaneously. This configuration recaptures the 50% portion of the light that previously passed through the 50/50 beam splitter and was lost. In addition, the recaptured light is used to illuminate the surface at an angle, thus enhancing the sensitivity of the system for detecting defocus errors.

Thus, the configuration of FIG. 4 is a combination that enables the detection of defects that are sensitive to illumination normal to the surface and the detection of defects that are sensitive to angular diffractive illumination. Like the other configurations, this configuration uses collimated light and the triple-wavelength, narrow-bandwidth filter.

FIG. 5 is a spectral response graph illustrating the relative response level of each channel of a typical 3-channel CCD camera such as the Sony XC-003/P CCD camera. Other types of cameras can also be utilized, including cameras sensitive to wavelengths outside the visible range.

Figure 6:
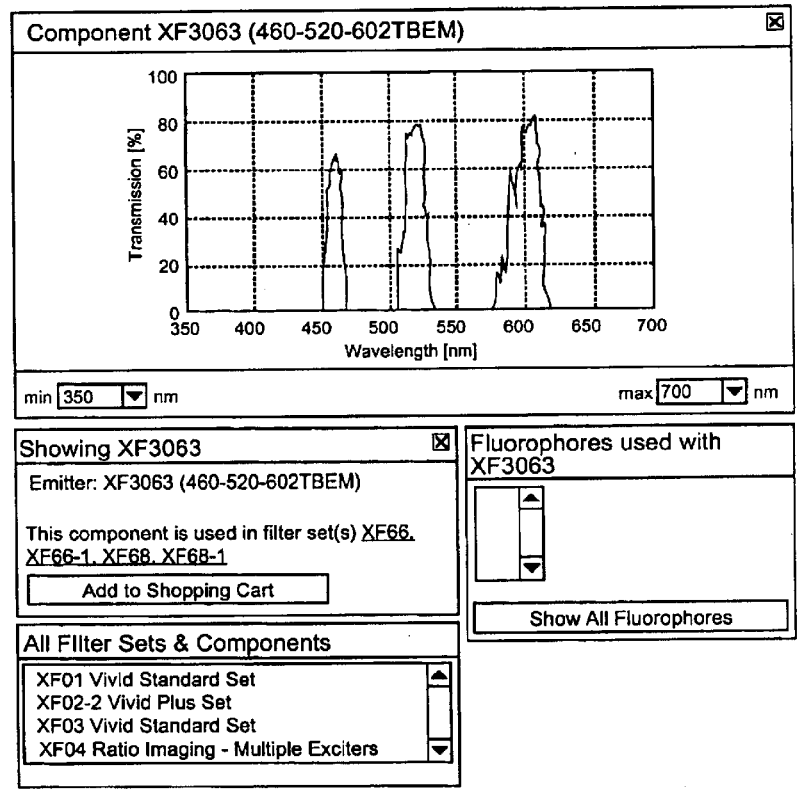
FIG. 6 is a light transmission graph illustrating the percentage transmission of light at three different wavelengths for an off-the-shelf triple bandpass filter suitable for use with the present invention.

FIG. 6 is a light transmission graph illustrating the percentage transmission of light at three different wavelengths for the Omega Optical XF3063 off-the-shelf triple-wavelength, narrow-bandwidth bandpass filter suitable for use with the present invention. Ideally, the triple bandpass filter is designed to pass light at discrete center frequencies equivalent to the frequencies where each channel of the CCD camera has maximum spectral response.

Figure 7:
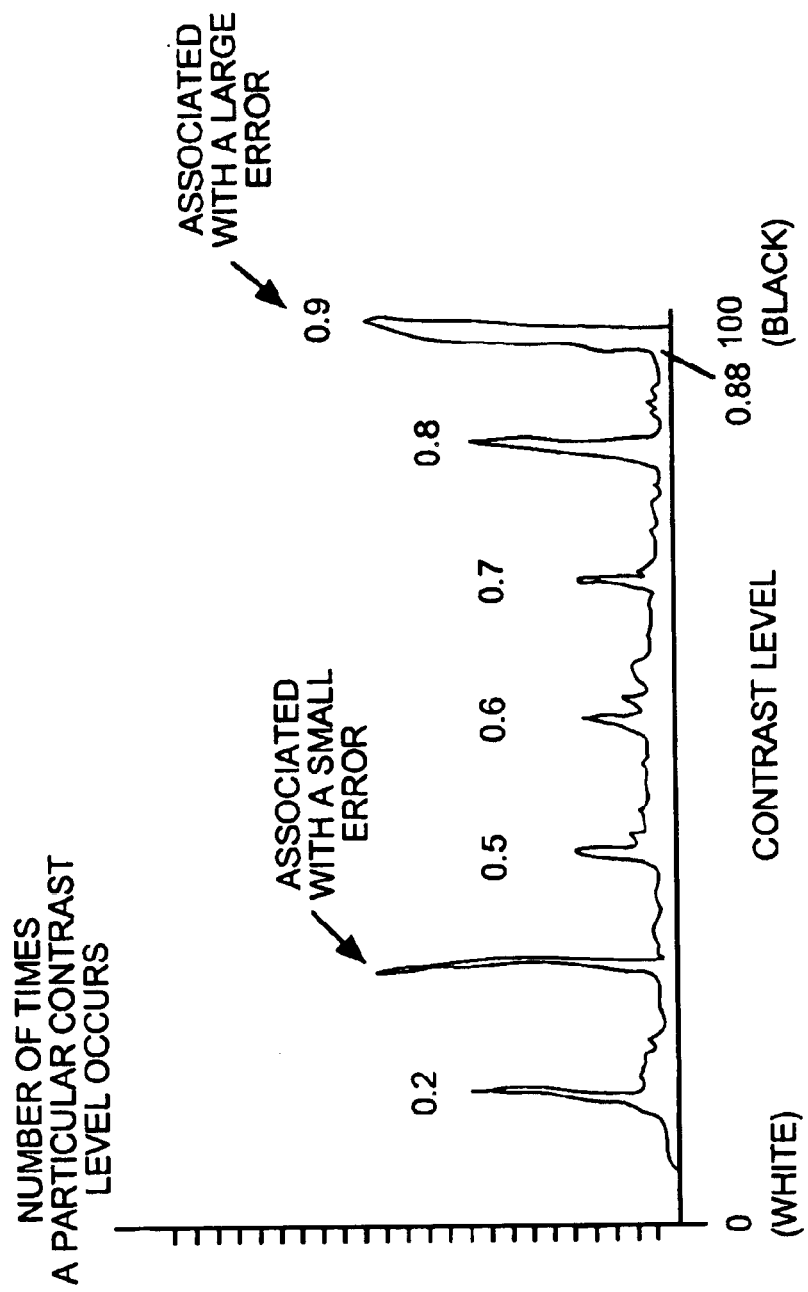
FIG. 7 is an image contrast graph resulting from a statistical analysis methodology that may be utilized with the present invention to classify defects according to their image contrast level.

FIG. 7 is an image contrast graph resulting from a statistical analysis methodology that may be utilized with the present invention to classify defects according to their image contrast level. The contrast level is shown on the horizontal axis on a scale from 0 to 100 (white to black). Higher contrast levels equate to larger defects on the wafer surface since larger defects cause a greater interruption to the diffractive effect of the surface structures. As a plurality of wafers are imaged with the present invention, the contrast levels from each wafer are used to build up the graph of FIG. 7. For example, after imaging 20 or more wafers, a spike of large amplitude may be generated at a contrast level of, for example, 0.88. The relatively high contrast level indicates that this particular type of defect is a relatively large defect. A calibration wafer on which defects of known sizes have been imaged may be utilized to quantify the size of the defect. The calibration wafer maybe created by microscopically measuring the size of particular defects for which the contrast level has been measured. For example, the image of the calibration wafer may reveal that a defect of 0.9 microns produces a contrast level of 0.88. Therefore, the size of the recorded defects can be determined by comparing the measured contrast levels with the levels recorded for the calibration wafer. The large amplitude of the spike indicates that this size of defect occurred on a greater number of wafers than other sizes of defects.

Another spike of large amplitude may be generated at, for example, a contrast level of 0.25. This contrast level indicates that this particular type of defect is a relatively small defect such as a 0.3 micron error. The large amplitude of the spike indicates that this size of defect occurred on a greater number of wafers than other sizes of defects. The width of a particular spike indicates that there is some degree of variability in the recorded contrast level for defects of a particular size. The graph in FIG. 7 indicates that there are seven major errors occurring on a repetitive basis on the wafers being inspected, some more often than others. The defects are periodic in structure, so there is most likely a systemic error in the wafer fabrication process that is causing these repetitive errors.

Figure 8:
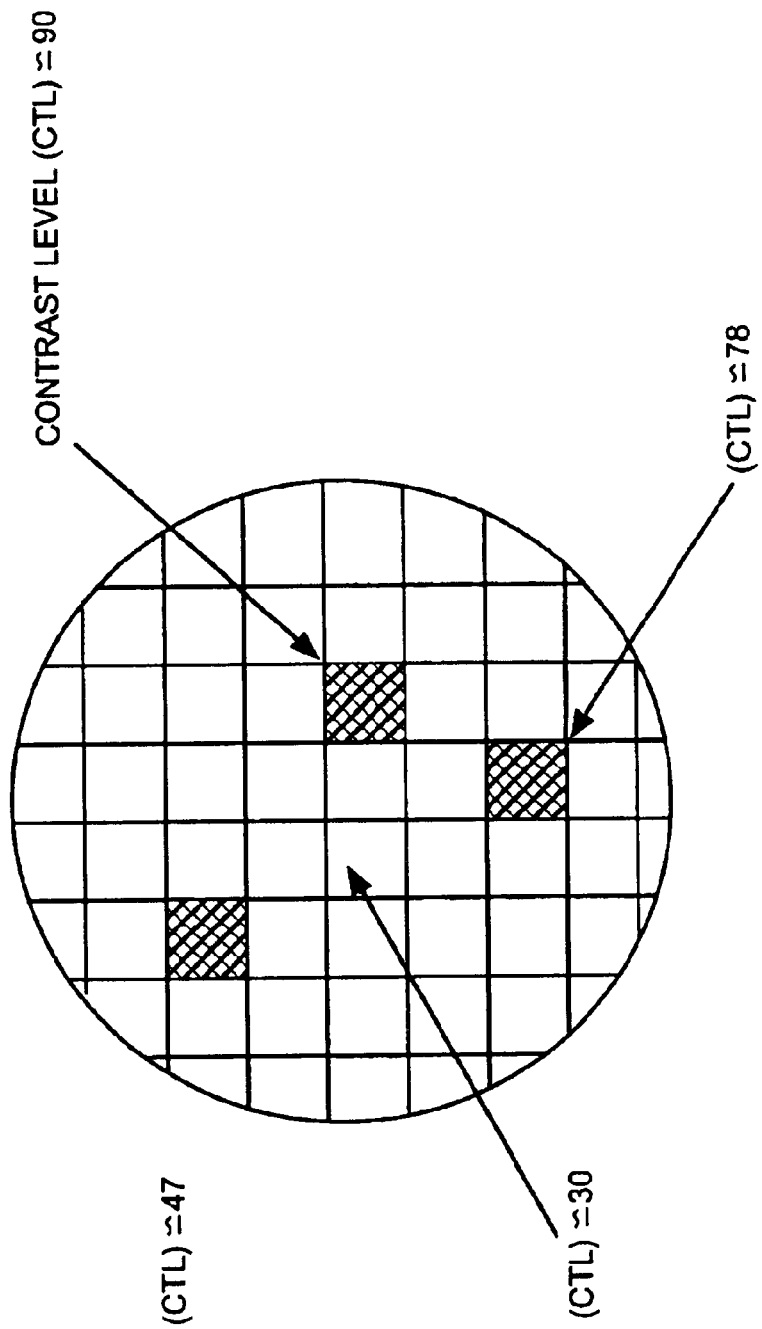
FIG. 8 is an illustrative drawing of an exemplary semiconductor wafer surface showing a plurality of die and their contrast levels recorded by the present invention, the recorded contrast levels from a plurality of wafers being used to generate the image contrast graph of FIG. 7.

FIG. 8 is an illustrative drawing of an exemplary semiconductor wafer surface showing a plurality of dice and their contrast levels as imaged by the present invention. At this particular magnification level, a defect on a die causes the contrast level of the entire die to be darker than the surrounding defect-free dice. The recorded contrast levels from a plurality of wafers are used to generate the image contrast graph of FIG. 7. If the wafer of FIG. 8 is a calibration wafer, defects of known sizes would be produced on different dice. The image would then be processed so that the contrast level of each die could be recorded for comparison with the dice on production wafers.

In summary, the present invention uses several techniques, either alone or in combination, to increase error-detection sensitivity. First, instead of using broad bandwidth illumination, the present invention uses a triple-wavelength, narrow-bandwidth bandpass filter which passes through illumination in three narrow bandwidths in the blue, green, and red wavelength ranges. Second, the three illumination wavelengths may be selected to match the peak sensitivity wavelengths of the three CCD camera channels. Alternatively, the illumination wavelengths may be selected to optimize the detection of particular types of defects, and the CCD camera may be designed to have peak specular response at the selected frequencies. Third, a collimator may be utilized to collimate the triple-wavelength, narrow-bandwidth incident light which then strikes the wafer surface normal to the surface. Fourth, the collimator may be used to collimate the triple-wavelength, narrow-bandwidth incident light which then strikes the object at an angle, thereby producing diffracted light leaving the wafer surface normal to the surface. Finally, the present invention may utilize all four techniques in combination.

It is thus believed that the operation and construction of the present invention will be apparent from the foregoing description. While the system and method shown and described has been characterized as being preferred, it will be readily apparent that various changes and modifications could be made therein without departing from the scope of the invention. For example, it should be clear to those skilled in the art that although the multi-wavelength, narrow-bandwidth filter has been described as a triple-wavelength narrow-bandwidth filter, the present invention may be practiced with a filter passing a fewer or greater number of narrow-bandwidth wavelengths. Additionally, although the filter and camera have been described as being in the visible light spectrum, it should be clear to those skilled in the art that the incident illumination may also be at wavelengths outside the visible spectrum such as ultraviolet or infrared wavelengths.

Additionally, whereas the use of specific commercially available components has been described in reference to the presently preferred exemplary embodiment of the present invention, the use of such components is merely illustrative, and such components may be replaced by other commercially available components or by custom designed components meeting the functional requirements described herein. Accordingly, all such modifications, extensions, variations, amendments, additions, deletions, combinations, and the like are deemed to be within the ambit of the present invention.

We claim:

1. A system for performing optical inspection of structures formed on a surface of a semiconductor wafer, said system comprising:

a light source for producing multiple narrow-band light spectra to illuminate the wafer surface; and a camera for capturing at least one image produced by light emanating from the illuminated wafer surface;

wherein the camera is a multi-channel camera having a plurality of sensitivity peaks associated with different frequencies of light, and wherein the multiple narrow-band light spectra are chosen such that their central frequencies correspond with the camera sensitivity peaks.

2. The system of claim 1, wherein the multiple narrow-band light spectra are produced by a multi-band filter.

3. A method for inspecting surface structure on a semiconductor wafer, said method comprising the steps of:

illuminating wafer surface using multiple narrow-band light spectra; and capturing an image associated with each separate of the separate spectral;

wherein the capturing step is performed suing a multi-channel camera having a plurality of sensitivity peaks associated with different frequencies of light, and wherein the multiple narrow-band light spectra are chosen such that their central frequencies correspond with the camera sensitivity peaks.

4. A method of inspecting the surface of an object to detect defects, if any, in structures formed on the surface, said method comprising the steps of:

receiving the object in an inspection stand;

illuminating the object with light from narrow-band spectra selected from different portions of the electromagnetic spectrum;

capturing at least one image associated with each of the illuminating spectra;

wherein the capturing step is performed suing a multi-channel camera having a plurality of sensitivity peaks associated with different frequencies of light, and wherein the multiple narrow-band light spectra are chosen such that their central frequencies correspond with the camera sensitivity peaks.

5. The method of inspecting the surface of an object to detect defects of claim 4, further comprising the steps of:

comparing the at least one captured image to the image of a calibrated object;

storing the captured image in a database;

displaying the at least one captured image; and generating a color defect map.

6. The method of inspecting the surface of an object to detect defects of claim 5, further comprising the steps of:

continuing the steps above for a plurality of wafers; and building an image contrast map.

* * * * *